United States Patent [19]

Schneider et al.

[11] Patent Number: 4,863,259
[45] Date of Patent: Sep. 5, 1989

[54] RAPID EYE MOVEMENT SLEEP STATE DETECTOR

[76] Inventors: Michael B. Schneider, 1718 W. Flournoy, #703, Chicago, Ill. 60612; Stephen R. Lloyd, 5642 N. Bernard, Chicago, Ill. 60659

[21] Appl. No.: 166,055

[22] Filed: Mar. 9, 1988

[51] Int. Cl.$^4$ ............................................. A61B 3/14
[52] U.S. Cl. .................................... 351/210; 351/209
[58] Field of Search ................. 351/209, 210; 128/733

[56] References Cited

U.S. PATENT DOCUMENTS

| | | |
|---|---|---|
| 2,724,109 | 11/1955 | Skolnick et al. |
| 3,379,885 | 4/1968 | Nork |
| 3,679,295 | 6/1972 | Newman et al. |
| 3,712,716 | 1/1973 | Cornsweet et al. |
| 3,804,496 | 4/1974 | Crane et al. |
| 3,863,243 | 1/1975 | Skolnick et al. |
| 3,889,251 | 6/1975 | Litman |
| 3,986,030 | 10/1976 | Teltscher |
| 3,992,087 | 11/1976 | Flom et al. |
| 4,109,145 | 8/1978 | Graf |
| 4,181,408 | 1/1980 | Senders |
| 4,300,818 | 11/1981 | Schachar |
| 4,450,437 | 5/1984 | Ho |
| 4,568,159 | 2/1986 | Baldwin |
| 4,648,052 | 3/1987 | Friedman et al. |

FOREIGN PATENT DOCUMENTS 3226096 2/1983 Fed. Rep. of Germany .
3229773 5/1983 Fed. Rep. of Germany .

OTHER PUBLICATIONS

R. Helfand et al., "REM/NREM Discrimination via Ocular and Limb Movement Monitoring: Correlation with Polygraphic Data and Development of a REM State Algorithm", *Psychophysiology*, vol. 23, No. 3, pp. 334–339 (1986).
T. Okuma, "Dream Detector and Automatization of REMP-Awakening Technique for the Study of Dreaming", *Psychophysiology* vol. 7, No. 3, pp. 508–515 (1971).
M. Cronin et al., "A Multichannel Hybrid System for Rapid Eye Movement Detection", *23rd A CEMB*, Washington, D.C. (Nov. 15–19, 1970).
R. Harper et al., "A New Technique for Long-Term Recording of Eye Movements in Infants", vol. 40, No. 1, *Electroencephalography and Clinical Neurophysiology*, pp. 109–112 (Jan. 1976).
A. Boukadoum et al., Publication entitled: "EOG--Based Recording and Automated Detection of Sleep Rapid Eye Movements: A Critical Review and Some Recommendations" *Psychophysiology*, vol. 23, No. 5, pp. 598–611, (1986).
Publication by Michael E. Long, "What is this thing called Sleep?", *National Geographic*, Dec. 1987, vol. 172 #6, p. 787.
Publication by T. Okuma, "Dream Detector and Comparison of Laboratory and Home Dreams Collected by REMP-Awakening Technique", *Advances in Sleep Research*, vol. 2, 1975, pp. 223–231 (1975).

*Primary Examiner*—Rodney B. Bovernick
*Assistant Examiner*—P. M. Dzierzynski
*Attorney, Agent, or Firm*—Hill, Van Santen, Steadman & Simpson

[57] ABSTRACT

A method and apparatus are provided in which an REM sleep state is accurately identified by detecting and counting a selectable number of eye movements within a selectable time interval. A body movement sensor is used to prevent false indications of REM sleep by inhibiting such indication upon sensing of body movement. An eye movement sensor which uses IR light transmission across an eye is disclosed.

36 Claims, 3 Drawing Sheets

RAPID EYE MOVEMENT SLEEP STATE DETECTOR

BACKGROUND OF THE INVENTION

1. Field of the Invention

The instant invention pertains generally to eye movement sensing and more particularly to a method and an apparatus for detecting a rapid eye movement sleep state.

2. Description of the Related Art

It is highly desirable to be able to accurately detect the presence of a rapid eye movement (REM) sleep state. Such detection is valuable for dream analysis, psychotherapy and other medical research.

A variety of methods and apparatus have been designed and applied in an attempt to accurately detect the presence of a rapid eye movement sleep state. An example is disclosed by R. Harper et al., in a publication entitled "A New Technique for Long-Term Recording of Eye Movements in Infants", Vol. 40, No. 1 Electroencephalography and Clinical Neurophysiology, pp. 109-112 (January 1976). In the article, Harper et al. disclose a disk-shaped eye piece which is taped over an eye, such as that of an infant, and which includes a gallium arsenide infrared-emitting diode and a silicon phototransistor mounted side by side to sense movement of one eye during sleep. The diode emits an IR beam which is reflected off of the eye lid or eye surface to the phototransistor. Both the diode and the phototransistor occupy a 0.5 cm$^3$ package. The device, which senses eye movements of either an open or closed eye, provides an output signal which is recorded on a chart recorder. The chart recorder is visually monitored to determine the presence of REM sleep.

In R. Helford, et al., "REM/NREM Discrimination via Ocular and Limb Movement Monitoring: Correlation with Polygraphic Data and Development of a REM State Algorithm," Psychophysiology, Vol. 23, No. 3, May 1986, pages 334-339, is disclosed a study involving piezoelectric transducers attached to the body in addition to eye movement sensors during sleep assessment. Movements were recorded on a polygraph and an algorithm is described generally for differentiating REM and non-REM periods.

In T. Okuma, et al. "Dream Detector and Automatization of REMP-Awakening Technique for the Study of Dreaming," Psychophysiology, Vol. 7, No. 3, November 1970, pages 508-515, is disclosed a device having electrodes for application to the face of a subject for dream detection. A block diagram in FIG. 1 shows the signal processing steps for the electrode output signals which leads to awakening of the subjects after a number of eye movements. The number of accumulated eye movements over a preset level were the only criteria used in dream detection.

M. Cronin, et al. disclose a system for detecting REM sleep in an article entitled "A Multichannel Hybrid System for Rapid Eye Movement Detection", 23rd A CEMB, Washington, D.C. (Nov. 15-19, 1970). In the system, electrodes are applied to an outer canthus or corner, of an eye. Electrical signals received thereby are filtered to retrieve signals corresponding to eye movements occuring over a period of from about 0.33 to 1.0 second. A threshold criterion is applied to each eye channel to record eye movements greater than a minimum amplitude. A digital output of the system is fed to a computer.

It would be an improvement in the art to provide a simple and inexpensive method and apparatus for automatically detecting and identifying REM sleep with a high degree of accuracy.

SUMMARY OF THE INVENTION

The instant invention provides a simple and inexpensive device for automatically distinguishing REM sleep with a high degree of accuracy. Moreover, the instant invention inhibits false REM sleep identification by detecting other physical characteristics which indicate that a person is not in REM sleep.

In the instant invention, individual eye movements that are detected by an eye movement sensor are counted by a counter. Preferably, only eye movements greater than a predetermined amplitude are counted. A timer connected to the counter times for a predetermined interval. If a predetermined number of eye movements are counted before expiration of the predetermined time interval, a determination is made that a person is in REM sleep, and accordingly, a signal is sent to an indicator for indicating the presence of REM sleep. If the predetermined time interval expires before the predetermined number of eye movements are counted, a determination is made that a person is in non-REM sleep, and a signal is sent to an indicator for indicating the presence for non-REM sleep. As soon as a determination of type of sleep is made, whether by expiration of the predetermined time interval, or by the eye movement counter counting the predetermined number of eye movements, both the eye movement counter and the timer are reset to zero and a new counting and timing cycle for redetermination of the presence of REM or non-REM sleep begins immediately.

In a further development, the invention may include a body movement sensor which, upon detecting gross body movement, inhibits the apparatus from indicating REM sleep for a predetermined period of time.

The eye movement sensor may be of any suitable type. However, it is preferable that the eye movement sensor use an infrared (IR) beam emitter and receiver to emit and receive, respectively, an infrared light beam on opposite sides of a cornea or anterior of any eyeball such that said infrared light beam is occluded whenever the cornea moves into its path upon movement of the eyeball.

It is therefore an object of the invention to provide a method and an apparatus for detecting a rapid eye movement sleep state which is simple and economical and yet highly accurate. It is an aspect of the invention that eye movements are counted within a predetermined time period and that a count of such eye movements within said time period greater than a preselected value indicates a rapid eye movement sleep state.

These objects and aspects will become apparent by reference to the description of the preferred embodiments and the attached drawings.

DESCRIPTION OF THE PREFERRED EMBODIMENTS

Figure 1:
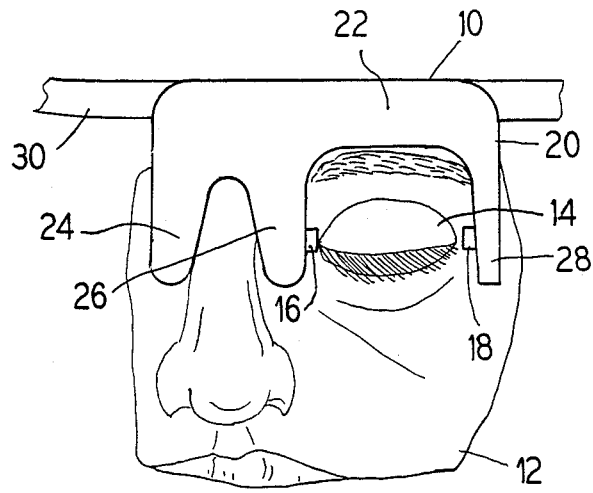
FIG. 1 is a front view of a person wearing an infrared emitting and sensing apparatus according to principles of the present invention for sensing eye movement.

In FIG. 1, an eye movement sensor 10 is worn on the face of a subject 12 for detecting movements of an eye 14 of the subject 12. The sensor 10 includes an infrared light beam emitter 16 and an infrared light beam receiver 18 mounted in a frame 20. The emitter 16 and receiver 18 emit and receive, respectively, an infrared light beam across the front of the eye 14. The frame 20 includes a cross-member 22 with downwardly depending fingers 24, 26 and 28. The fingers 24 and 26 extend downward on opposite sides of a nose of the subject 12 to support the frame 20 and maintain it in position on the subject 12 relative to the eye 14. The emitter 16 and receiver 18 are secured facing each other on the fingers 26 and 28, respectively, at opposite sides of the eye 14. A band 30 fixed to either side of the frame 20 encircles the subject's head and secures the sensor 10 in place.

Figure 2:
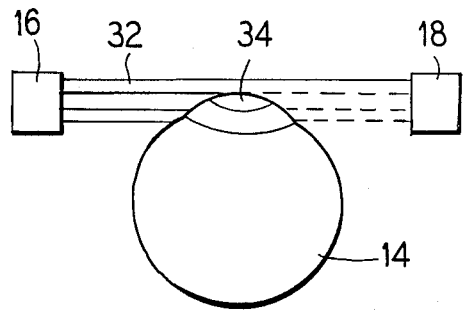
FIG. 2 is a diagramatic representation in horizontal cross-section of the infrared eye movement sensor of FIG. 1 showing an infrared light beam being transmitted across and partially interrupted by an eye.

As shown in FIG. 2, an infrared light beam 32 is transmitted by the emitter 16 toward the receiver 18. When the sensor 10 is in the position shown in FIG. 1, the beam 32 is transmitted across the front of the eye 14. Whether the lid of the eye 14 is open or closed, a protruding anterior portion 34 of the eyeball 14 protrudes into the light beam 32 thereby causing the sensor 10 to perceive the extent to which the beam 32 is blocked. The protruding anterior portion 34 of the eye 14 is, of course, the cornea of the eye 14. When the eye 14 is open, the cornea 34 itself blocks a portion of the beam 32. However, since the present invention is intended to measure sleep states, the lid of the eye 14 will generally be closed and the cornea 34 will make the characteristic protrusion of the eyelid. For purposes of the present invention, all references hereinafter to the cornea or protruding anterior portion 34 are deemed to cover both the cornea of the open eye, as well as the protrusion of the lid caused by the cornea of the closed eye.

Figure 3:
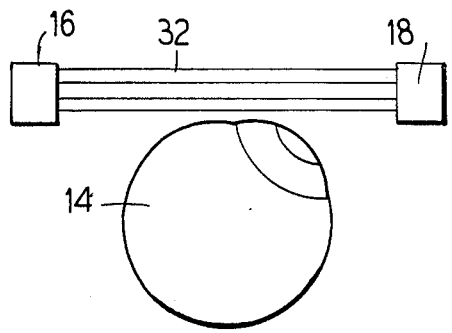
FIG. 3 is a diagrammatic cross-section of the sensor of FIG. 1 in which the eyeball is shown in a position such that the infrared light beam is not broken by the eye.

As shown in FIG. 3, movement of the eye 14 in its socket results in a change of the extent to which the beam 32 is blocked by the cornea 34. In FIG. 3, blockage of the beam 32 is completely eliminated by the extreme rotation of the eye 14 shown. While such extreme rotation may seldom occur, it can be appreciated that nearly any movement of the eye 14 will result in a detectable variation in the intensity of the beam 32 reaching the receiver 18. This results in corresponding variations in the electrical signal at the output of the receiver 18.

If it is desired to decrease the exposure to the eye of infrared emissions, for example, for safety or other reasons, the beam 32 can either be decreased in intensity or can be pulsed so that the average power transmitted across the eye is less. Such pulsing of the beam 32 can be accomplished by any known beam pulsing means.

While a preferred eye sensor has been described for use with the invention, a variety of other sensors may be used, such as those which detect reflection of infrared light from an eye or those which use piezoelectric, electro-occular, mechanical, or other sensors.

Figure 4:
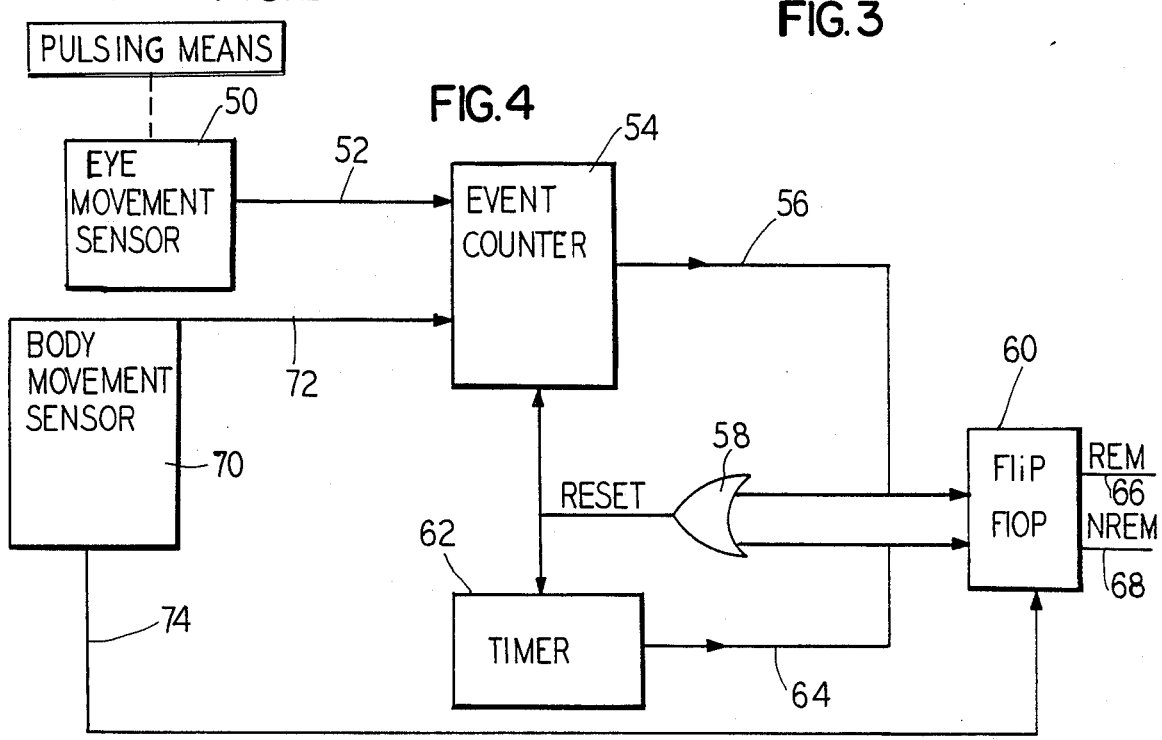
FIG. 4 is a functional block diagram of an REM state detection device embodying principles of the instant invention and including the eye movement sensor of FIG. 1.

In FIG. 4 there is shown a diagram including fundamental aspects of the invention. In the invention, an eye movement sensor 50, which may be the above-described sensor unit 10, senses eye movement and sends a representative signal along a path 52 to an event counter 54. Preferably, the eye movement sensor 50 emits a pulse signal, wherein each pulse represents a single movement of an eyeball. The event counter 54 then maintains a running total of the pulses emitted by the eye movement sensor 50.

When the running total in the event counter 54 is high enough, the event counter 54 will emit a signal over path 56 to reset circuitry 58 and to REM sleep indicating circuitry 60. Simultaneously, a timer circuit 62 times for a preselected time interval. At the end of each interval, a signal is emitted by the timing circuit 62 over path 64 to both the reset circuitry 58 and to the REM sleep indicating circuit 60.

With respect to the reset circuitry 58, whenever a signal is received from either the event counter 54 or the timing circuit 62, the event counter 54 and the timing circuit 62 will be reset. Thus, as can be seen, whenever the event counter 54 counts a predetermined number of eye movements within the preselected time interval, a REM sleep state will be indicated. At the same time, both the timing circuit 62 and the event counter 54 will be reset so as to enable a redetermination as to the existence of the REM sleep state. Similarly, whenever the timing circuit 62 times the preselected time interval, both the event counter 54 and the timing circuit 62 will be reset so as to enable a redetermination of an existence of a REM sleep state. If the preselected time interval passes and the event counter 54 has not counted a sufficient number of eye movements, the signal transmitted from an output 64 of the timer 62 to the REM sleep state indicating circuit 60 will cause such circuit 60 to indicate the absence of an REM sleep state. The sleep state indicating circuit 60 in the illustrated embodiment is a flip-flop with an REM indicating output 66 and a non-REM indicating output 68.

Also shown in FIG. 4 is the optional use of a body movement sensor 70. The body movement sensor 70 may comprise any of a number of motion sensing switches. Upon sensing body movement, the body movement sensor emits a signal over path 72 to the event counter 54 to prevent counting of eye movements for a predetermined period of time. Simultaneously, a signal is emitted by the body movement sensor 70 over a path 74 to the indicating circuit 60 to cause the indicating circuit 60 to be reset to indicate, at the output 68, the absence of a REM sleep state.

The use of the optional body movement sensor 70 is important because there are many times when an REM sleep state appears to exist if only the movement of an eye is considered. However, if body movement is present, a true REM sleep state does not exist. Thus, by sensing body movement, false readings as to the existence of a REM sleep state are eliminated.

Another optional feature of the invention shown in FIG. 4 is the use of a pulsing means 76 for the eye movement sensor 50. The pulsing means 76 may be used to pulse the infrared beam 32 of the eye movement sensor 50 and may also be used to synchronize the beam sensor with the pulse beam. It is, of course, possible to apply pulsing to other types of sensors as well.

Figure 5:
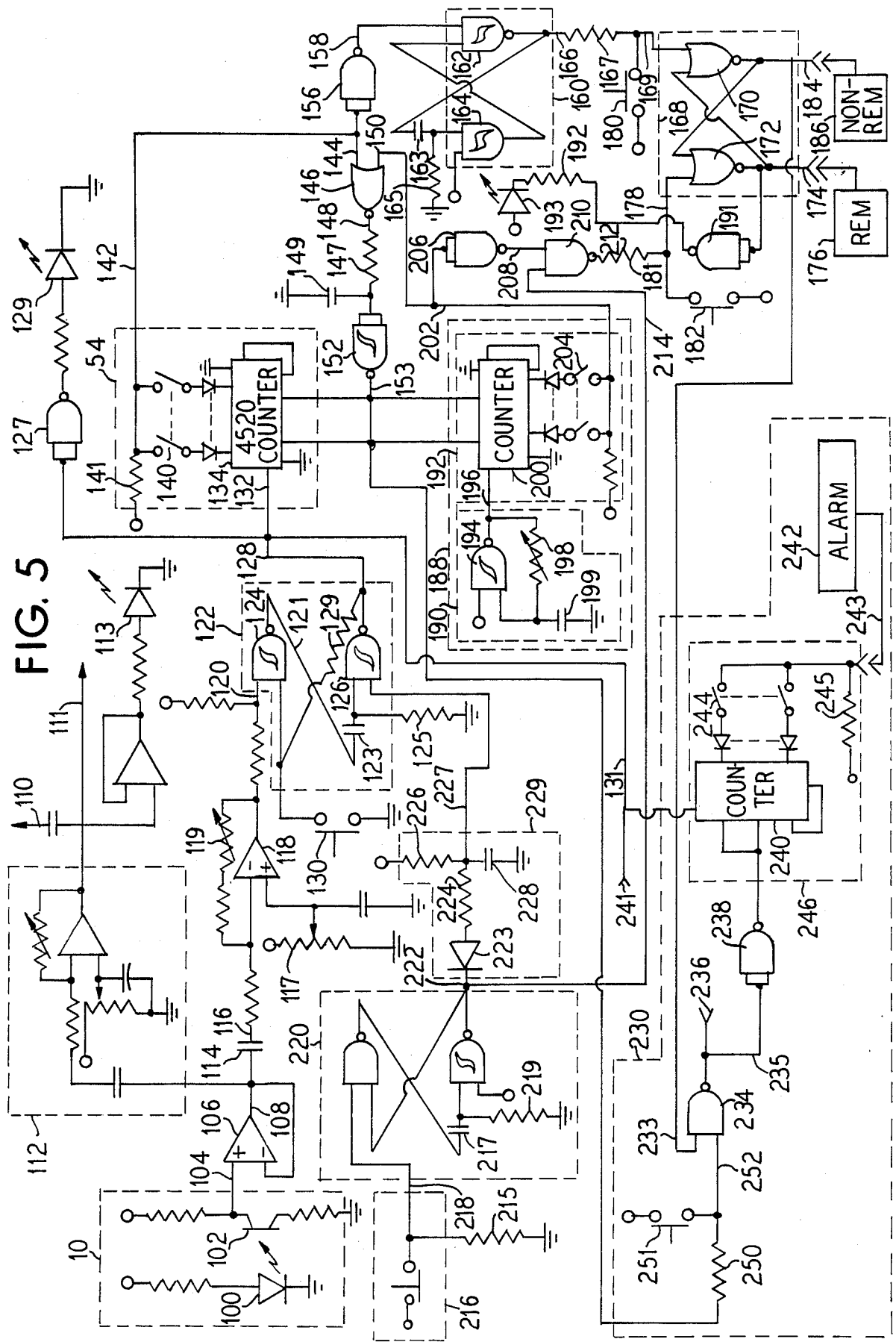
FIG. 5 is a circuit diagram of one embodiment of the device of FIG. 4 constructed according to principles of the invention.

With reference now to FIG. 5, a preferred embodiment of the invention will be described.

Shown in the schematic diagram of FIG. 5 is the use of an IR eye movement sensor 10 described previously. As can be seen, an IR light emitting diode 100 serves as the IR emitter 16, and phototransistor 102 serves as the IR receiver, 18. In the presence of eye movement, the amount of IR light reaching a phototransistor 102 will vary, as discussed above, and a signal output by the phototransistor 102 at an output 104 will vary accordingly.

A voltage follower 106 formed by an operational amplifier isolates the eye movement sensor 10 from loading effects in the circuitry of the detector as is well known in the art. A signal corresponding to the signal 104 is produced at an output 108.

An alternating current (AC) component of the signal at 108 is made available for external monitoring and/or processing at a lead 110 after appropriate shaping by circuitry 112 as is well known in the art. A direct current (DC) component is made available at lead 111. An output of circuitry 112 is also used to drive an LED 113 to indicate the presence of eye movement.

An AC component of the signal at 108 is extracted by a capacitor 114 and made available at lead 116. The signal on lead 116 is fed into an operational amplifier 118 which includes potentiometer 117 and variable resistor 119 to provide an adjustable baseline level and an adjustable gain, respectively. A signal output by differential amplifier 118 is provided at lead 120. As will be recognized by one of skill in the art, the differential amplifier 118 is triggered only by rapidly changing signals and not by slowly changing signals. Thus, the preferred embodiment detects only rapid eye movements that are indicative of REM sleep and ignores slower eye movements.

The signal at lead 120 is then fed into a monostable multivibrator 122 made up of two NAND Schmitt trigger gates 124 and 126. Gates 124 and 126 are arranged in the cross-lead flip-flop configuration as is known by those skilled in the art. Insertion of capacitor 123 and resistor 125 in cross-lead 121 causes the flip-flop to function as a monostable multivibrator. A negative going pulse at lead 120 causes the flip-flop to change state. However, the resulting state is maintained for a finite time determined by the values of capacitor 123 and resistor 125. Following the change in state (output low at lead 128, output at lead 121 high), capacitor 123 begins charging. As capacitor 123 charges, electrical potential at the junction between capacitor 123 and resistor 125, initially high, begins dropping. When this potential drops to the negative going threshold of the input of Schmitt trigger NAND gate 126, output at lead 128 returns to a high state. As a consequence, the output at lead 128 goes low for a specific period of time, regardless of the length of the negative going pulse received at lead 120 during the timing cycle. Thus, monostable multivibrator 122 conditions signals received at lead 120, lengthening pulses shorter than the specified period and shortening pulses longer than the specified period, providing such conditioned signal at output lead 128. Values of capacitor 123 and resistor 125 are chosen so as to provide a conditioned low signal at lead 128 approximately 1/10 second, in response to a negative going signal at lead 120. A switch 130 is included and may be closed to manually cause the monostable multivibrator 122 to produce a conditioned low pulse at lead 128. Resistor 129 which provides for one cross-lead connection, prevents loading of the output at lead 128 when switch 130 is closed.

The signal at the lead 128 is inverted and buffered in a gate, such as NAND gate 127, and transmitted to an LED 129 which serves as a visual indication of the presence of a signal on the output 128 of monostable multivibrator 122.

The signal at the output 128 is also coupled to an input 132 of the event counter circuit 54 which includes an integrated circuit (IC) counter 134. The IC 134 is readily available off-the-shelf and is designated generically as a CD4520 counter IC. The IC contains two 4-stage binary counters. The counters are cascaded in the present application by connecting the "Q4" output of the first counter to the "ENABLE" pin of the second counter (pin function names are those of the manufacturer).

The counter IC 134 maintains a cummulative count of each time the signal at the lead 132 goes low. As the cummulative count advances, corresponding output pins of the counter 134 go high. These output pins are connected through diodes to program switches 140. Until high signals appear at output pins connected to all closed ones of program switches 140 (these are preset to a given count which is believed to be indicative of a REM sleep state), lead 142 is held low. When high signals appear all output pins connected to closed ones of program switches 140, lead 142 is brought high by pull-up resistor 141 as is known in the art.

For purposes of clarity, only two of the switches 140 are shown, although eight such switches and diode combinations are provided. In one embodiment, the switches 140 appear at output leads 3, 4, 5, 6, 11, 12, 13, 14, as so designated by the manufacturer, of the CD4520 IC 134. The number of eye movements required to produce a signal on the lead 142 is selected by setting the switches 140 to the corresponding binary number.

The signal at the lead 142 is coupled to an input 144 of a NOR gate 146. A signal output from the NOR gate 146 at lead 148 is normally high unless a high signal is present at either the input 144 or an input 150.

When output 148 has been high for a sufficiently long time, capacitor 149 is fully charged through resistor 147. In this fully charged state, capacitor 149 presents a high signal to both inputs of NAND Schmitt trigger gate 152, which acts as an inverter to provide a low output signal. When the counter 134 receives a sufficient number of low pulses at the lead 132, a high signal appears at the lead 142 and a low signal appears at the lead 148.

When the low signal appears at lead 148, capacitor 149 begins discharging through resistor 147. When the voltage across capacitor 149 drops below the negative going threshold of one or both of the inputs of NAND Schmitt trigger gate 152, the output of this gate goes high. This high signal is used to reset the cumulative count in the counter IC 134 to zero.

The signal at the lead 148 is inverted by the NAND gate 152 and the inverted signal at lead 153 is used to reset the cumulative count in the counter IC 134 to zero. The combination of resistor 147, capacitor 149, and NAND Schmitt trigger gate 152 serve the purpose of producing a time delay in the reset signal, allowing the signal on lead 142 to remain high for sufficient time to permit the effects of the high signal on lead 142 to be propagated through other circuitry.

In addition to input 144, the signal output at the lead 142 of the event counter 54 is input into an inverter 156. An output signal of the inverter 156 is available at lead 158 and is fed into an input of monostable multivibrator 160 made of NAND Schmitt trigger gates 162 and 164, and capacitor 163 and resistor 165, arranged and functioning in a manner identical to monostable multivibrator 122 described above. Monostable multivibrator 160 provides a high signal pulse at lead 166 each time lead 142 goes high (and lead 158 goes low).

The signal at the lead 166 is coupled through resistor 167 to an input of a flip-flop 168 which is made of two NOR gates 170 and 172, inter-connected as is known in the art. A signal output from the flip-flop 168 at a lead 174 is used to indicate the ascertainment of a REM sleep state, such as by a REM indicator 176. The signal at the output lead 174 goes high (REM sleep detected) whenever the signal at the lead 166 goes high (REM sleep detected) unless a signal at an input lead 178 goes high, i.e., whenever a preselected time interval has expired or when body movement has been sensed as will be explained below. Switches 180 and 182 are provided to allow one to manually set the inputs 169 and 178, respectively, to a high state, in order to manually change the state of the flip-flop for testing purposes.

Resistors 167 and 181 prevent shorting of the outputs of gates 162 and 210, respectively, when switches 180 or 182, respectively, are closed. The flip-flop 168 provides the final REM sleep-no REM indicated decision.

Depending on the various input states to the flip-flop 168, some previously described and others to be described shortly, the flip-flop 168 will react by changing its output signals at the REM indicating output 174 and a non-REM indicating output 184. These outputs 174 and 184 can be used to drive a variety of devices, such as displays or alarms (not shown). The flip-flop 168 will continuously indicate either a REM sleep state or non-REM state, through non-REM indicator 186, and REM indicator 176 until a change in state is determined.

The devices which may make use of the signals at the outputs 174 and 184 are almost limitless. As an example, the signals at the outputs 174 and 184 may be used to turn on tape recorders and an alarm to allow a sleeper to awake and record a dream. Alternatively, the signals may be used to turn on indicator lights or audio or other indicators to alert the sleeper or an observer of REM sleep status or to influence the content of sleeper's dreams.

A simple count of eye movement is generally not enough to positively determine the presence of a REM sleep state. REM sleep is characterized by a large number of eye movements within a short time interval, e.g., one minute. Thus, to detect REM sleep, the arrangement of FIG. 5 also includes a provision for measuring the passage of time and determining the number of eye movements in a predetermined interval.

As can be seen in FIG. 5, a timing circuit 188 is provided which includes a time base generator circuit 190 and a counter circuit 192. The time base circuit 190 is well known in the art. A Schmidt trigger 194, in conjunction with capacitor 199 and variable resistor 198, acts as an oscillator and preferably produces a low pulse on an output 198 at every second. Alternate time base frequencies may be used by adjusting variable resistor 198. Other time base means may be provided instead, including crystal controlled oscillators and the like.

The pulsed timing signal at the output 196 is fed into an event counter 192 which counts the pulsed signal. The event counter 192 may be formed by the same type of circuit as the event counter 54, and so functions similarly. An output signal at lead 202 will go high whenever a cummulative count in the event counter 200 reaches a value programmed via switches 204.

The signal at the output lead 202 is fed into the input 150 of the reset NOR gate 146. As described earlier, when the signal at the input 150 goes high (indicating a preselected time interval has elapsed), the signal at the point 148 goes low. The signal at the point 148 is inverted and time-delayed by the NAND Schmitt trigger 152 in conjunction with resistor 147 and capacitor 149, as previously described. The inverted signal at the lead 153 is then used to reset the event counter 134 and the time counter 200 to zero for a subsequent redetermination of the presence or absence of REM sleep.

The signal output at 202 is also fed into a NAND inverter 206 to produce an inverted signal at lead 208 which is in turn input into the NAND gate 210. A signal from output led 212 of the NAND gate 210 is low only when the signal at the lead 202 is low (indicating that the preselected time interval has not passed) and a signal on lead 214 is high (indicating that a body movement has not been detected, as will be described later).

The signal at the lead 212 is fed through resistor 181 into the input 178 of the flip-flop 168. When the signal at the input 178 goes high (indicating that the time interval has elapsed), the output signal at the REM indicating output 174 will go low (no REM sleep detected). At the same time, the signal at the non-REM indicating output 184 goes high to indicate that no REM sleep was detected.

LED 193 with resistor 192 and inverting NAND gate 191 provides a means of visually indicating the state of flip-flop 168.

Also included in the arrangement shown in FIG. 5 is circuitry for inhibiting possible false readings of REM sleep state existence by sensing the sleeper's movements. It has been determined that persons do not generally make large motor movements when in an REM sleep state.

A motion sensing switch 216 is provided, as is shown in FIG. 5. Such a switch may be of any type, e.g., a pressure sensitive switch, piezoelectric switch, a mercury switch, a vibration sensitive switch, etc., so long as it adequately senses large motor body movement and emits a corresponding signal.

The body motion sensing switch 216 is connected between a power supply (not shown) and an input 218 of a monostable multivibrator 220, so that upon opening of the switch 216 (body movement sensed), a low pulse signal through pull-down resistor 215 will be present at the input 218. The low pulse signal from the switch 216 is lengthened by the pulse lengthener monostable multivibrator 220 so that a low pulse of specific length is made available at lead 222. Monostable multivibrator 220 functions in a manner identical to the functioning of monostable multivibrator 122, which was described previously.

The signal from the monostable multivibrator 220 at lead 222 is fed into the NAND gate 210 over the lead 214 and is subject to a logic NAND function with the inverted output on the lead 208 of the timing circuit counter 200. The resulting output signal at the lead 212 is then fed into the flip-flop 168 which makes the final REM-no REM decision, as discussed previously. Thus, when body motion is sensed, the resulting low pulse signal in lead 214 forces a high pulse signal at output 212 of NAND gate 210 and consequently to input 178 of flip-flop 168. The outputs of flip-flop 168 then indicate the absence of a REM state.

Low pulse signals from output 222 of monostable multivibrator 220 also activate a timing cycle in timer circuit 229. Timer circuit 229 functions as follows:

In the steady state (when no low pulses have been received for some period of time), output at lead 222 is a steady high, Capacitor 228 is fully charged through resistor 226 connected to the positive voltage supply (not shown), thus presenting a high input through lead 227 to one input of NAND Schmitt trigger gate 126. This high input enables gate 126 and permits it to function as part of monostable multivibrator 122 as described above.

When a low pulse appears at output 222 of monostable multivibrator 220, capacitor 228 is quickly discharged through resistor 224 and forward-biased switching diode 223. The values of resistors 219 and 224 and capacitors 217 and 228 are chosen so that the width of the low pulse at output 222 is of sufficient length to adequately discharge capacitor 228 during the duration of the pulse. Capacitor 228 is adequately discharged when the voltage appearing in lead 227 is below the negative going threshold of the input of Schmitt trigger NAND gate 126. Upon termination of the low pulse at output 222 of monostable multivibrator 220, output 222 returns to a high state. Because the voltage at lead 227 is substantially lower than the high signal at output 222, diode 223 is reverse biased and no current flows through diode 223 or resistor 224. However, capacitor 228 begins re-charging through resistor 226, which is connected to the positive supply voltage (not shown). Resistor 226 is chosen to have a value substantially larger than resistor 224. As a consequence, the re-charging of capacitor 228 will be correspondingly longer than its discharge through resistor 224 and diode 223. The re-charging constitutes a timing cycle which continues until the voltage at lead 227 reaches the positive going threshold of the input of Schmitt trigger NAND gate 126. Until this timing cycle is completed, the voltage in lead 227 is seen as an effective low signal by Schmitt trigger NAND gate 126. This effective low signal forces output 128 of monostable multivibrator 122 to maintain a high state for the duration of the aforementioned timing cycle, regardless of other inputs. Thus, for the duration of the timing cycle, monostable multivibrator 122 is disabled from transmitting eye movement signals to counting circuit 54.

Large body movements may result in shifts of position of eye movement sensors. This may result in artifactual eye movement signals, which are actually gross body movements. Thus, the disabling of monostable multivibrator 122 for a time period following body movments prevents the transmission of these artifactual signals to the counting circuit 54. It is, of course, also possible to provide no time delay following body movements, although time delays in a range of between one and 100 seconds are preferred.

The REM/non-REM indicating outputs of flip-flop 186 may be used for a variety of purposes. For example, it may be desired to awaken a sleeper for purposes of obtaining a report of his REM dream content. One method for doing this would be to awaken the sleeper in REM sleep after a pre-programed cumulative number of eye movements has occurred. Circuitry for accomplishing this purpose is shown in FIG. 5 as REM counter 230.

Negative going pulses representing eye movements at output lead 128 of monostable multivibrator 122 are transmitted via lead 131 to the enable input (manufacturer's designation) of CD4520 integrated circuit 246. Counter integrated circuit 246 in conjunction with programming switches 244 and pull-up resistor 245 form an event counter 246 which functions in a manner identical to event counter 54. Positive going reset pulses on lead 153 are transmitted via resistor 250 to input lead 252 and NAND gate 234. If a high signal is present on another input lead 233 of NAND gate 234, then positive going pulses on lead 252 are inverted to negative going pulses on lead 235. These negative going pulses are again inverted to positive pulses by NAND gate 238, connected with both inputs connected together to function as a simple inverter. Positive pulses output from inverter 238 are transmitted to reset inputs of counter IC 240.

Input lead 233 of NAND gate 234 is connected to "NREM" output 184 of flip-flop 168. When output 184 is low, indicating presence of a REM state, the low signal on input 233 of NAND gate 234 forces the output of gate 234 into a continuous high state and reset pulses appearing on input 252 are not transmitted through the gate. When output 184 is high, indicating presence of a non-REM state, reset pulses are transmitted (inverted) through gate 234.

When a REM state is present, event counter 54 is continually being reset each time it reaches the pre-programmed count set by switches 140. This is necessitated by the need for repeated testing for the presence or absence of a REM state. By contrast, event counter 246 is not reset during the REM state. Consequently, event counter 246 is able to count the cumulative number of eye movements occurring during the entire duration of the REM state. During the NREM state, event counter 246 is reset synchronously with resets of event counter 54.

Outputs 241 and 236 are provided for count pulse and reset pulse outputs to an external device. One possibly useful external device which could make use of these outputs would be an external counter, which counts and resets synchronously with event counter 246. Such a counter may be of many types. One purpose for such a counter would be to provide a visual display of the eye movement count for research purposes. A monolithic counter module with a visual display suitable for such purposes is sold as "SUBCUB-1" by Red Lion Controls, Inc.

Switch 251 is connected between the positive voltage supply and lead 252 in order to provide a means of manually resetting counter 246 and an external counter, if used. Resistor 250 serves to prevent short circuiting of the output of gate 152 and resetting of counter 54 and 192 when switch 251 is closed.

When event counter 246 reaches the count pre-set by programming switches 244, output 243 is pulled high by pull-up resistor 245, connected to the positive voltage supply. Output 243 may be used to control another device 242, which may be a means for generating an alarm device for awakening the sleeper. With such an alarm device, the sleeper can be awakened from the REM sleep state after a specific number of eye movements, in order to obtain a report of dream content.

Figure 6:
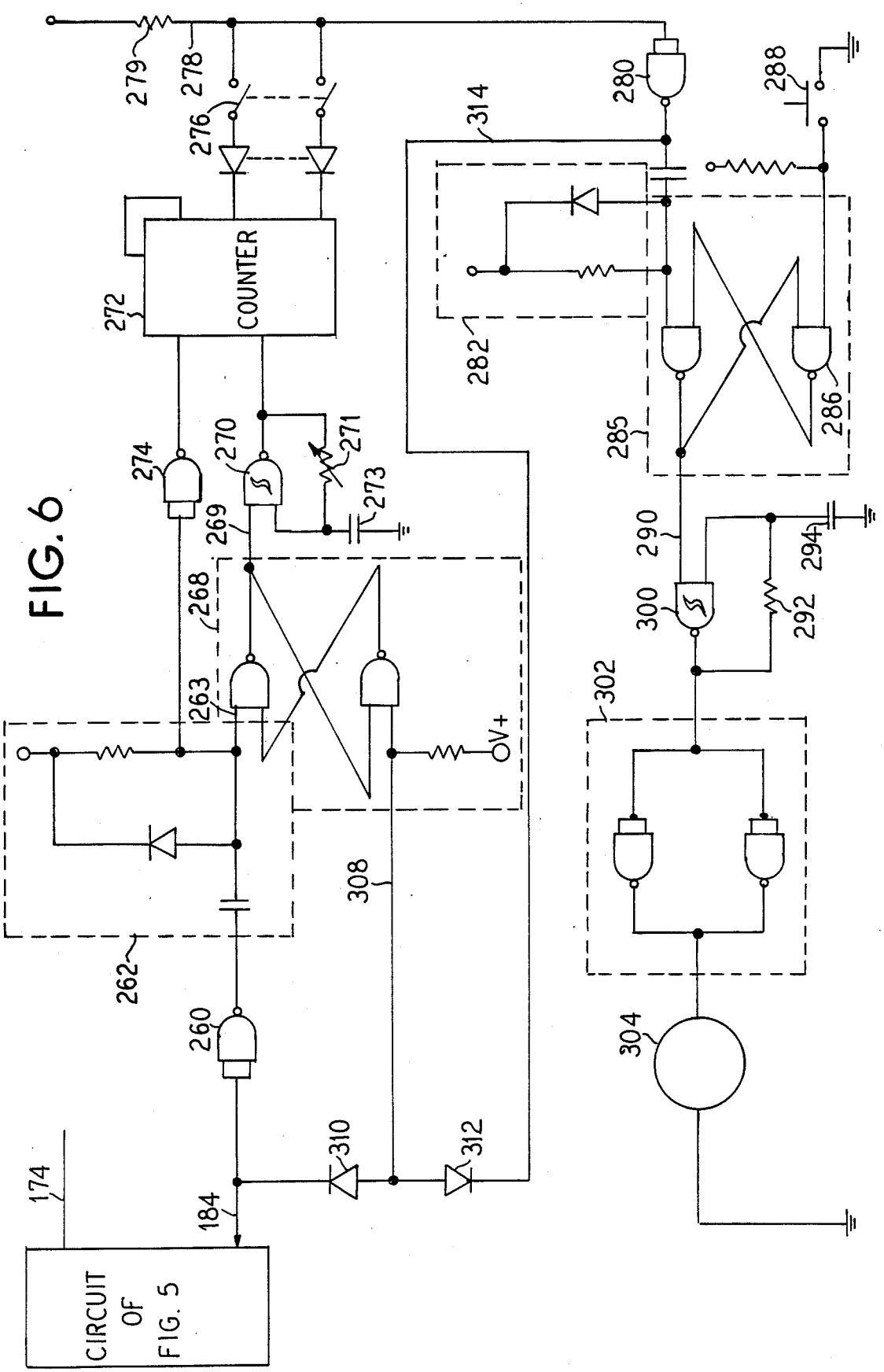
FIG. 6 is a circuit diagram of one embodiment of REM/NREM state output indicator.

Another method for awakening a sleeper for a report of his REM sleep dream content would be to awaken the sleeper within a pre-programmed time following termination of the REM sleep stage. FIG. 6 depicts a circuit, which, when connected with the circuit of FIG. 5, will accomplish this end.

When a patient is producing a certain number of rapid eye movements within a certain period of time, the flip-flop 168 indicates a "REM state." "REM" output 174 is at a high state and "NREM" output (184) is at a low state.

Output 184 is presented to both inputs of NAND gate 260, connected to function as an inverter. Inverter 260, thus presents a high signal to the input of differentiator circuit 262 (composed of a resistor, diode, and capacitor, as is known in the art).

When NREM output 184 goes to a high state, the differentiator circuit 262 presents a momentarily low signal to input 263 of set-reset flip-flop 268 composed of two NAND gates connected as is known in the art.

The low signal at input 263 causes flip-flop 268 to change state, thus presenting an enabling high signal on lead 269 to NAND Schmitt trigger gate 270, which is connected as a gate astable oscillator as is known in the art. Once enabled, the oscillator formed by gate 270 sends timed negative going pulses to the enable (manufacturer's designation) input of counter IC 272 (CD4520). Preferably, the values of capacitor 273 and resistor 271 are chosen so that oscillator 270 presents pulses at a rate of one per second.

The momentarily low signal from differentiator 262 is also presented to NAND gate 274, connected as an inverter. Inverter 274 converts the momentarily low signal to a momentarily high signal which is presented to the reset inputs of CD4520 counter IC 272. This reset pulse ensures that each counting cycle of counter 272 is initialized with a count of zero. The time counter 272 utilizes programming switches 276 in a manner identical to counters 54 and 192, described previously.

When the count on counter 272 reaches the pre-programmed setting on switches 276, lead 278 is pulled high through pull-up resistor 279. The high signal on lead 278 is inverted by NAND gate 280 connected as an inverter. Thus, inverter 280 presents a low signal to differentiator circuit 282 and lead 314. When the input to differentiator 282 initially goes low, the differentiator 282 transmits a momentary low pulse to flip-flop 285, composed of two NAND gates connected as is known in the art. This slow pulse changes the state of the flip-flop 285, causing an enabling high signal to appear at input 290 to NAND Schmitt trigger gate 285 connected with a resistor 292 and a capacitor 294 to form a gated astable oscillator as is known in the art. The values of resistor 282 and capacitor 294 are chosen so that the frequency of square wave pulses produced by astable oscillator 300 is approximately 1 to 3 Hz. These pulses are input to inverting buffer alarm driver 302 composed of two NAND gates connected in parallel. With two NAND gates connected in parallel, sufficient current is provided to drive piezo-electric alarm buzzer 304. With each low pulse from astable oscillator 300, a high signal is provided by the output of alarm driver 302. This high signal turns on piezo-electric alarm buzzer 304 for the duration of the pulse. A number of suitable piezo-electric alarm buzzers are commercially available. One such suitable alarm is sold in the United States by the Radio Shack Division of Tandy Corporation as catalog number 273-060.

The sounding alarm can be turned off by closing switch 288, thus presenting a low signal to an input of NAND gate 286 of flip-flop 285. This low signal causes the flip-flop to change state. A low signal appears at lead 290, disabling astable oscillator 300 and forcing it to a resting high output state. This high signal is inverted by alarm driver 302 to a low (zero voltage) signal and no current flows to piezo-electric alarm buzzer 304.

When counter 272 reaches the pre-programmed setting on switches 276, further counting is prevented by the previously mentioned low signal on lead 314. This low signal pulls input 308 of flip-flop 268 low through switching diode 312. The low input on input 308 resets flip-flop 268, putting a disabling low signal on gating lead 269 of astable oscillator 270 and forcing said oscillator into its resting high output state. In the absence of low pulses from oscillator 270, counter 272 remains at the count pre-programmed on switches 276.

Similarly, lead 308 is also pulled low (disabling timebased oscillator 270 in the same manner) through diode 310, whenever there is a return to a low state on lead 184 (indicating a return to REM sleep).

NAND Schmidt trigger gates are used widely throughout the circuits of FIGS. 5 and 6. This simplifies construction and reduces the number of integrated circuit packages required. In many cases, however, the characteristics of a Schmidt trigger are not necessary to the functioning of a gate at a particular location. Also, both inputs of some NAND gates are tied together, for example, to form a NOT or inverter function. Such gates can, of course, be replaced by other elements.

In general, those gates involved in timing or oscillating functions should be Schmidt trigger gates, and are shown as such in FIGS. 5 and 6 by being marked with a hysteresis symbol.

The NAND Schmidt trigger gates of one exemplary embodiment are available as a type CD4093 integrated circuit, while those NAND gates not having the Schmidt trigger function are available as type CD4011 chips. Simple inverters can be used from CD4069 or CD4049 chips. All such chips are in CMOS technology. The counters are dual CMOS hexidecimal counters, type CD4520, with pins 3, 4, 5, 6, 11, 12, 13, and 14, as designated by the manufacturer, each tied to a series diode and switch combination. In all cases, both counting sections of each CD4520 integrated circuit are chained to create a single 8 bit binary counter. This is accomplished by connecting the high bit output (pin 6) of the first counter section to the "enable" input (pin 10) of the second counter section. Negative going pulses to be counted are entered via the "enable" input (pin 2) of the first counter section. "Clock" inputs (pins 1 and 9) of the two counter sections are connected to ground.

Diodes used in differentiator circuits and with programming switches are commercially available as type 1N4148 switching diodes. Other types of diodes might also be used by one skilled in the art.

Thus, a REM sleep state detector has been described which is relatively simple and inexpensive to build, yet highly accurate. Moreover, provisions have been made to reduce false readings in the presence of body movement during sleep and to permit detection of various activities within the detector.

While a preferred embodiment has been described, modifications which fall within the scope and spirit of the invention may become apparent to those skilled in the art. It is intended that such modifications be covered as well by the attached claims.

We claim:

1. An apparatus for detecting sleep states, comprising:

means for detecting movement of an eye and for transmitting an eye movement signal in response thereto; and means for receiving and evaluating said eye movement signal including: timing means for timing a predetermined interval, counting means for maintaining a cumulative count of eye movements indicated by said eye movement signal, and establishing a count signal whenever said cumulative count reaches a predetermined number, and indicating means for indicating existence of said predetermined number of detected eye movements within said predetermined interval.

2. An apparatus as set forth in claim 1, further including reset means coupled to said counting means for resetting said counting means in response to a timing signal from said timing means upon elapse of said predetermined interval.

3. An apparatus as set forth in claim 1, further comprising:
reset means coupled to said timing means for resetting said timing means in response to receipt of a counting signal from said counting means indicating that a predetermined number of detected eye movements have been counted.

4. An apparatus as set forth in claim 3, wherein said reset means resets said timing means and said counting means upon receipt of a timing signal from said timing means and upon receipt of a counting signal from said counting means.

5. An apparatus as set forth in claim 4, wherein said timing means includes means for emitting time base signals at selectable time base intervals and means for counting said time base signals and emitting a timing signal upon reaching a selected count of said selected time base signals.

6. An apparatus as set forth in claim 1, wherein said indicating means includes means for indicating the passage of said predetermined time interval without detection of said predetermined number of eye movements.

7. An apparatus as set forth in claim 6, further comprising:
means for awakening a sleeper within a second predetermined interval following the passage of said predetermined time interval without detection of said predetermined number of eye movements.

8. An apparatus as claimed in claim 7, wherein said indicator means emits an audible sensory signal.

9. An apparatus as claimed in claim 7, wherein said indicator means emits a vibrating sensory signal.

10. An apparatus as claimed in claim 7, wherein said indicator means emits a visible sensory signal.

11. An apparatus as claimed in claim 7, wherein said indicator means is activated when said count signal is received before said time signal to indicate the existance of a predetermined sleep state.

12. An apparatus as claimed in claim 7, wherein said indicator means is activated when said time signal is received before said count signal to indicate the end of a predetermined sleep state.

13. An apparatus as set forth in claim 1, further comprising:
means for sensing movement of a body; and
means for inhibiting said indicating means upon sensing of body movement by said sensing means.

14. An apparatus as set forth in claim 1, wherein said means for detecting movement of an eye comprises means for transmitting and receiving an electromagnetic beam adjacent an eye where movement of the eye results in detectable variations of the electromagnetic beam.

15. An apparatus as set forth in claim 14, further comprising:
means for pulsing said electromagnetic beam.

16. An apparatus as set forth in claim 1, wherein said means for detecting movement of an eye comprises a piezoelectric sensor for application in a region of the eye.

17. An apparatus as set forth in claim 1, wherein said means for detecting movement of an eye comprises an electro-occular eye movement sensor.

18. A method for sensing sleep states, comprising the following steps:
sensing movements of an eye;
counting said sensed eye movements;
emitting a count signal whenever a predetermined number of eye movements are sensed;
timing a predetermined selected interval;
emitting an interval signal upon elapse of said predetermined interval; and
indicating existence of a sleep state whenever said count signal occurs prior to the occurrence of said interval signal.

19. A method as set forth in claim 18, including a further step of:
resetting said counted eye movements to zero after emission of said interval signal.

20. A method as set forth in claim 18, including a further step of:
restarting said timing step at zero after emission of said count signal.

21. A method as set forth in claim 18, including further steps of:
restarting said counting step at zero after emission of one of said count signal and said interval signal, and restarting said timing step at zero after emission of one of said count signal and said interval signal.

22. A method as set forth in claim 21, including a step terminating indication of existence of said sleep state whenever said interval signal is emitted prior to said count signal.

23. A method as set forth in claim 22, further including the step of:
awakening a sleeper within a predetermined interval following said step of terminating indication of existence of said sleep state.

24. A method as set forth in claim 18, further including steps of:
sensing body movement; and
inhibiting indication of said sleep state after said body movement is sensed.

25. A method as set forth in claim 18, wherein said step of sensing movements of an eye includes transmitting an electromagnetic beam across said eye.

26. An apparatus for detecting sleep states, comprising:
an eye movement sensor which emits a movement signal upon sensing a movement of an eye;
a counter coupled to said eye movement sensor which maintains a cummulative count of movements sensed by said eye movement sensor and which emits a count signal whenever said cummulative count reaches a selected number;
a timer which times an interval and which emits a time signal whenever said interval has elapsed; and a sleep state indicator circuit coupled to said counter and said timer which emits a signal whenever said count signal is received before said time signal.

27. An apparatus as set forth in claim 26, including reset circuitry for resetting said cummulative count to zero and said timer to zero whenever one of said count signal and said time signal is emitted.

28. An apparatus as set forth in claim 27, wherein said indicator circuit comprises a digital flip-flop arrangement to maintain said emitted signal until said time signal is received prior to said count signal.

29. An apparatus as set forth in claim 28, including a sensor connected to sense body movement and to emit a signal upon sensing of body movement, said body movement sensor being coupled to said indicator circuit to inhibit emission of said output signal.

30. An apparatus as set forth in claim 29, wherein said eye movement sensor comprises an emitter and receiver for an electromagnetic transmitted across an eye.

31. An apparatus as claimed in claim 26, further comprising:
    indicator means for emitting a sensory signal to be sensed by a sleeper.

32. An apparatus as claimed in claim 26, further comprising:
    means for recording being activated by said sleep state indicator circuit.

33. An eye movement sensor, comprising:
    means for transmitting an electromagnetic beam across an eye including:
        means for emitting an electromagnetic beam across an eye such that movement of said eye will cause said to protrude varyingly into said electromagnetic beam thereby causing the amount of electromagnetic energy transmitted in said electromagnetic beam to vary, and
        means for receiving said electromagnetic beam; and
    means for generating a signal in response to said varying amounts of electromagnetic energy received by said means for receiving.

34. An eye movement sensor as set forth in claim 33, including means for maintaining said means for emitting and means for receiving said electromagnetic beam on opposite sides of an eye.

35. An eye movement sensor as set forth in claim 33, wherein said means for emitting comprises an infrared light emitting diode, and said means for receiving comprises a phototransistor.

36. An apparatus as set forth in claim 35, wherein said means for awakening includes:
    a timer connected to emit an alarm initiation signal within said second predetermined interval; and
    an audible indicator connected to emit an audible signal upon receipt of said alarm initiation signal.

* * * * *